United States Patent [19]

Crutcher et al.

[11] Patent Number: 5,254,291
[45] Date of Patent: Oct. 19, 1993

[54] SURFACTANT COMPOSITIONS

[75] Inventors: Terry Crutcher; Joe D. Sauer; Kim R. Smith; James E. Borland, all of Baton Rouge, La.

[73] Assignee: Ethyl Corporation, Richmond, Va.

[21] Appl. No.: 698,551

[22] Filed: May 10, 1991

[51] Int. Cl.$^5$ ............................................. C11D 1/831
[52] U.S. Cl. ................................................ 252/545
[58] Field of Search ........................... 252/548, 545

[56] References Cited

U.S. PATENT DOCUMENTS

| | | | |
|---|---|---|---|
| 4,247,425 | 1/1981 | Egan et al. | 252/548 |
| 4,595,526 | 6/1986 | Lai | 252/545 |
| 4,857,213 | 8/1989 | Caswell et al. | 252/545 |
| 4,997,641 | 3/1991 | Hartnett et al. | 252/173 |

FOREIGN PATENT DOCUMENTS 62-135598  6/1987  Japan ................................ 252/548

Primary Examiner—Michael Lewis
Assistant Examiner—Stuart L. Hendrickson
Attorney, Agent, or Firm—Patricia J. Hogan

[57] ABSTRACT

Surfactant mixtures capable of providing a foamability performance equal to that of any of the components of the mixture at a lower cost comprise (1) an ethoxylated fatty alcohol, (2) a fatty acid alkanolamide, and (3) an alkyl sulfate.

5 Claims, No Drawings

SURFACTANT COMPOSITIONS

FIELD OF INVENTION

This invention relates to surfactant compositions and more particularly to such compositions which permit the attainment of desirable characteristics economically.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of anionic surfactants in these compositions permits the attainment of desirable characteristics, including good foamability, it would be beneficial to find other surfactants which could provide equal performance at a lower cost. However, other known surfactants, such as amine oxides, betaines, and alkanolamides, are either more costly than the anionic surfactants or give poorer performance, e.g., smaller foam volume, when substituted for the anionic surfactants.

It is sometimes advantageous to use mixtures of surfactants in cleaning compositions when the surfactants can serve different functions, e.g., one serving to improve foamability and another serving to adjust viscosity. Heretofore, however, it was not thought that the use of (A) a less costly surfactant which, by itself, gives poor performance in a particular regard, e.g., foamability, in admixture with (B) a more costly surfactant which, by itself, gives good performance in the same regard, could permit the retention—or even the improvement—of the good performance of the more costly surfactant while reducing the total cost of surfactant used. The most common result of using such an admixture is to provide a performance which is intermediate to the performances of the different surfactants.

SUMMARY OF INVENTION

It has been found that a mixture of an ethoxylated fatty alcohol, a fatty acid alkanolamide, and an alkyl sulfate can provide a foamability performance equal to that of any of the components of the surfactant mixture at a lower cost.

DETAILED DESCRIPTION

Ethoxylated fatty alcohols which may be used in the practice of the invention are compounds corresponding to the formula $Z(OCH_2CH_2)_mOH$ in which Z is an alkyl group containing 4-30 carbons, preferably 10-18 carbons, and m is an integer of 1-50, preferably 2-15. Particularly preferred ethoxylated fatty alcohols are the lauryl ethoxylate in which m is 6 and the ethoxylate of a mixture of $C_{12}$ and $C_{14}$ alcohols in which m is 6; but other ethoxylates corresponding to the formula, such as those formed from one or more alcohols such as butanol, isobutanol, hexanol, octanol, decanol, dodecanol, tetradecanol, pentadecanol, hexadecanol, octadecanol, eicosanol, docosanol, tetracosanol, and triacontanol, are also utilizable.

Fatty acid alkanolamides which may be used in admixture with the ethoxylates are the known nonionic surfactants usually designated as superamides, i.e., alkanolamides obtained by reacting a fatty acid, usually a fatty acid containing 10-18 carbons, with an alkanolamine in equal proportions. The preferred alkanolamide is cocodiethanolsuperamide.

The alkyl sulfate employed in conjunction with the ethoxylate and alkanolamide may be any of the alkyl sulfates conventionally employed as surfactants. Such anionic surfactants are usually alkali metal or ammonium salts of alkyl sulfates in which the alkyl groups contain 10-18 carbons, and sodium lauryl sulfate is generally preferred.

The three-component ethoxylate/alkanolamide/alkyl sulfate mixtures of the invention appear to have the advantage of cost-effectiveness, i.e., providing any given level of foam at less cost than any of their components, regardless of the proportionation of the components. However, some of the mixtures, generally mixtures containing about 25-95% by weight of the alkyl sulfate, have the additional advantage of being synergistic in their foamability, i.e., providing a level of foam greater than can be provided by any of their components. Thus, the preferred mixtures contain about 5-90% by weight of the ethoxylate, about 10-90% by weight of the alkanolamide, and about 10-90% by weight of the alkyl sulfate. Mixtures containing 75% by weight of the ethoxylate, about 12% by weight of the alkanolamide, and about 13% by weight of the alkyl sulfate are particularly cost-effective.

The invention is advantageous in that it provides novel surfactant mixtures which can provide acceptable levels of foam more economically than the individual components of the mixture. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following example is given to illustrate the invention and is not intended as a limitation thereof. Unless otherwise specified, quantities mentioned in the example are quantities by weight.

EXAMPLE

Varying amounts of (A) a lauryl ethoxylate containing six —$OCH_2CH_2$— groups per molecule, (B) cocodiethanolsuperamide (SA), and (C) sodium lauryl sulfate were dissolved in hard water (200 ppm as $CaCO_3$) to provide solutions having a total surfactant content of 0.1%.

The foamability of the surfactants was then measured by (1) placing 30 mL of each of the solution in a 100 mL stoppered graduated cylinder, (2) inverting the cylinder ten times, (3) measuring the foam height, (4) repeating steps 1-3 twice, and (5) calculating the average of the three measurements.

The proportions of ethoxylate, SA, and sulfate used in preparing each of the solutions and the foam heights obtained from them are shown in the Table below.

TABLE

| Ethoxylate (%) | SA (%) | Sulfate (%) | Foam Height (mL) |
|---|---|---|---|
| 100 | 0 | 0 | 28 |
| 0 | 100 | 0 | 17 |
| 0 | 0 | 100 | 30 |
| 13 | 12 | 75 | 33 |
| 25 | 25 | 50 | 38 |
| 33 | 34 | 33 | 33 |
| 50 | 25 | 25 | 35 |
| 25 | 50 | 25 | 29 |
| 75 | 12 | 13 | 30 |
| 12 | 75 | 13 | 27 |

What is claimed is:

1. A surfactant mixture consisting of (1) about 5-75% by weight of an ethoxylated fatty alcohol corresponding to the formula $Z(OCH_2CH_2)_mOH$ in which Z is an alkyl group containing 10-18 carbons and m is an integer of 2-15, (2) about 10-75% by weight of a fatty acid alkanolamide, and (3) about 10-75% by weight of an alkyl sulfate.

2. The surfactant mixture of claim 1 wherein the fatty acid moiety of the alkanolamide and the alkyl group of the sulfate contain 10-18 carbons.

3. The surfactant mixture of claim 2 wherein the ethoxylated fatty alcohol is a lauryl ethoxylate containing six $—OCH_2CH_2—$ groups per molecule, the alkanolamide is cocodiethanolsuperamide, and the alkyl sulfate is sodium lauryl sulfate.

4. The surfactant mixture of claim 3 containing at least 25% by weight of the alkyl sulfate.

5. A surfactant mixture consisting of 75% by weight of a lauryl ethoxylate containing six $—OCH_2CH_2—$ groups per molecule, about 12% by weight of cocodiethanolsuperamide, and about 13% by weight of sodium lauryl sulfate.

* * * * *